(12) United States Patent  (10) Patent No.: US 7,396,342 B2
Wang et al.  (45) Date of Patent: Jul. 8, 2008

(54) SAFETY SYRINGE FOR TAKING BLOOD

(75) Inventors: Shih-Chun Wang, Chia-Yi (TW); Kiwi Yuan, Taipei (TW); Jia-Ming Chang, Banciao (TW)

(73) Assignee: Biotop Holding Co., Ltd., George Town, Grand Cyman (KY)

( * ) Notice: Subject to any disclaimer, the term of this patent is extended or adjusted under 35 U.S.C. 154(b) by 195 days.

(21) Appl. No.: 11/286,393

(22) Filed: Nov. 25, 2005

(65) Prior Publication Data

US 2007/0123821 A1    May 31, 2007

(51) Int. Cl.
    *A61M 5/00*    (2006.01)
(52) U.S. Cl. ........................... 604/110; 600/576
(58) Field of Classification Search .......... 604/110, 604/192, 195, 198, 403; 600/576–578
    See application file for complete search history.

(56) References Cited

U.S. PATENT DOCUMENTS

| | | | |
|---|---|---|---|
| 4,150,666 A | 4/1979 | Brush | |
| 4,320,769 A | 3/1982 | Eichhorn | |
| 4,367,746 A | 1/1983 | Derechinsky | |
| D277,132 S | 1/1985 | Hayashi | |
| 4,738,827 A | 4/1988 | Pierotti | |
| 4,788,986 A * | 12/1988 | Harris | 600/576 |
| 4,854,318 A | 8/1989 | Solem | |
| 4,871,355 A | 10/1989 | Kikkawa | |
| 4,900,310 A | 2/1990 | Ogle | |
| D307,796 S | 5/1990 | Hanifl | |
| 4,947,863 A | 8/1990 | Haber | |
| 4,991,601 A | 2/1991 | Kasai | |
| 5,000,167 A | 3/1991 | Sunderland | |
| 5,030,209 A | 7/1991 | Wanderer | |
| 5,069,225 A | 12/1991 | Okamura | |
| D323,710 S | 2/1992 | Kasai | |
| 5,090,420 A | 2/1992 | Nielsen | |
| 5,120,311 A | 6/1992 | Sagstetter | |
| 5,131,405 A | 7/1992 | Burns | |
| 5,188,119 A | 2/1993 | Sunderland | |
| RE34,223 E * | 4/1993 | Bonaldo | 604/192 |
| 5,217,025 A | 6/1993 | Okamura | |
| 5,219,333 A | 6/1993 | Sagstetter | |
| 5,222,505 A | 6/1993 | Burns | |
| 5,273,161 A | 12/1993 | Sagstetter | |
| D350,195 S | 8/1994 | Poulsen | |
| 5,356,392 A | 10/1994 | Firth | |
| 5,409,112 A | 4/1995 | Sagstetter | |
| 5,409,443 A | 4/1995 | Zabriskie | |

(Continued)

*Primary Examiner*—Nicholas D. Lucchesi
*Assistant Examiner*—Victoria P Campbell
(74) *Attorney, Agent, or Firm*—Bacon & Thomas, PLLC

(57) ABSTRACT

A safety syringe for taking blood has a hollow barrel having a bottom open end, a top end, a rectangular hole defined in the top end to have two opposite long sides and two opposite short sides, a needle hub detachably connected between the two opposite short sides of the rectangular hole and having a first needle extending from an elliptical body into an interior of the hollow barrel and a second needle extending away from the hollow barrel, a cap rotatably connected to the top end of the hollow barrel and having a notch defined through a periphery of the cap to receive therein the elliptical body so that the second needle extends out of the cap after in combination with the cap and an enclosure detachably enclosing the second needle for protection.

6 Claims, 6 Drawing Sheets

U.S. PATENT DOCUMENTS

| | | |
|---|---|---|
| 5,485,854 A | 1/1996 | Hollister |
| 5,577,653 A | 11/1996 | Bieker |
| 5,583,043 A | 12/1996 | Sakariassen |
| RE35,539 E * | 6/1997 | Bonaldo .................... 600/573 |
| 5,749,504 A | 5/1998 | Bieker |
| 5,776,078 A | 7/1998 | Wardlaw |
| 5,797,490 A | 8/1998 | Fujii et al. |
| 5,868,772 A | 2/1999 | LeVaughn |
| 5,876,355 A | 3/1999 | Suzuki |
| 5,961,473 A | 10/1999 | Fujii |
| 6,024,710 A | 2/2000 | Miller |
| 6,024,727 A * | 2/2000 | Thorne et al. .............. 604/195 |
| 6,074,883 A | 6/2000 | Kelly |
| 6,080,366 A | 6/2000 | Kelly |
| 6,110,160 A | 8/2000 | Farber |
| 6,126,903 A | 10/2000 | Preston |
| 6,146,337 A | 11/2000 | Polidoro |
| 6,171,262 B1 * | 1/2001 | Bonaldo .................... 600/573 |
| 6,213,952 B1 | 4/2001 | Finarov |
| 6,274,087 B1 | 8/2001 | Preston |
| 6,375,027 B1 | 4/2002 | Thomas |
| 6,400,971 B1 | 6/2002 | Finarov |
| 6,520,948 B1 | 2/2003 | Mathias |
| 6,733,465 B1 | 5/2004 | Smutney |
| D492,776 S | 7/2004 | Nilsson |
| 6,835,316 B2 | 12/2004 | Dolecek |
| RE39,107 E * | 5/2006 | Shaw ........................ 604/110 |

* cited by examiner

SAFETY SYRINGE FOR TAKING BLOOD

BACKGROUND OF THE INVENTION

1. Field of the Invention

The present invention relates to a syringe, and more particularly to a safety syringe that can safely retract a used needle back into a barrel and prevent users from being hurt by the used needle.

2. Description of Related Art

There are two types of conventional syringes used for taking blood, one has a hollow barrel, a plunger and a needle hub, and the other has a short holder, an inner needle and a needle hub. The plunger of the first type is received inside the hollow barrel, and the needle hub is connected to the hollow barrel. The short holder of the second type has an outside surface, a bottom surface and an inner space. The needle hub is mounted on the bottom surface of the outside surface and the inner needle mounted on inner space and connects to the needle hub.

When using the first type of the conventional syringe, a user takes blood into the hollow barrel then inserts the collected blood into a vacuum tube. When using the second type of the conventional syringe, the needle hub is inserted into a vein and a vacutainer is connected to the inner needle inside the short holder. Because of the attraction of the vacutainer and the blood pressure, blood will flow into the vacutainer slowly.

However, the used needles extended outside the hollow barrel or the short holder of the conventional syringes will easily hurt users after taking blood. To keep nurses, doctors or health workers who deal with discarded syringes from being injured or infected by used needles, a safety syringe for taking blood is needed. In another aspect, the short holder of the second conventional syringe is too easily reused to hold a new needle and unscrupulous staff may be tempted to reduce costs in this way whereby serious unsanitary conditions will be met.

To overcome the shortcomings of conventional syringes, the present invention provides a safety syringe to mitigate or obviate the aforementioned problem.

SUMMARY OF THE INVENTION

The primary objective of the present invention is to provide a safety syringe for taking blood. The safety syringe for taking blood in accordance with the present invention comprises a hollow barrel, a needle hub, a cap and an enclosure.

The hollow barrel has a bottom open end in communication with an interior of the barrel so that a tube for containing therein a sample is able to be received in the hollow barrel via extending through the bottom open end of the hollow barrel. A bottom cap is foldably formed on a periphery defining the bottom open end of the barrel. A rectangular hole and a sectorial hole are both defined in a top end of the barrel to communicate with each other. The needle hub has an elliptical body so as to define two opposite long sides and two opposite short sides respectively sandwiched between the two long sides. A first needle is provided on a first side of the hollow body for extending through a membrane of a tube which is securely received in the barrel and a second needle is provided on a second side of the hollow body to be opposite to the first side for extending into a skin of a living creature, such as a human.

When using the syringe in accordance with the present invention, the needle hub partially extends into the barrel and rotate for a predetermined degrees so that the needle hub can be securely held inside the barrel for application and after usage, the needle hub is rotated again to allow the needle hub to fall into the barrel so that accidental injury to the persons who deal with discarded material is avoided.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
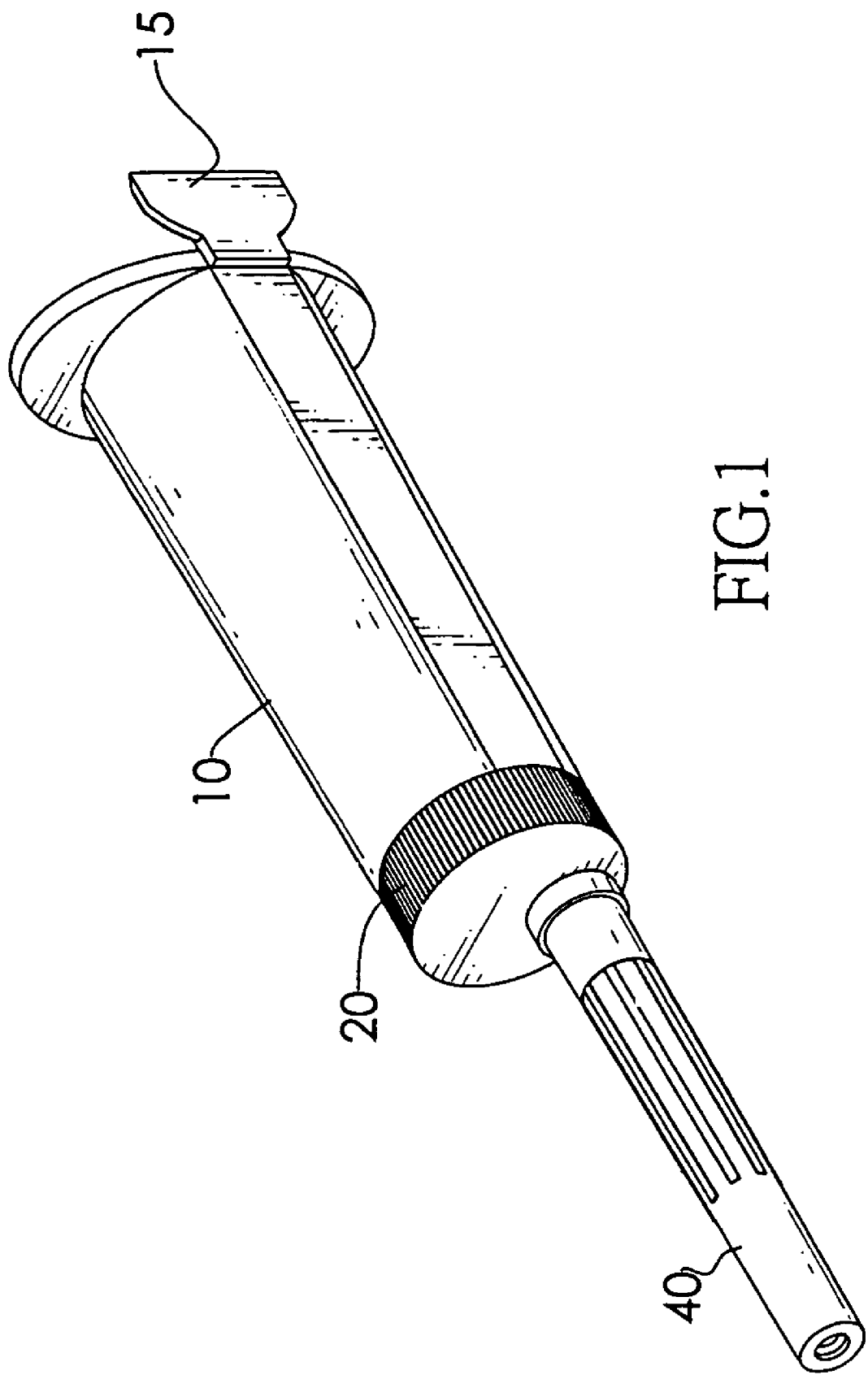
FIG. 1 is a perspective view of a preferred embodiment of a safety syringe for taking blood in accordance with the present invention.
Figure 2:
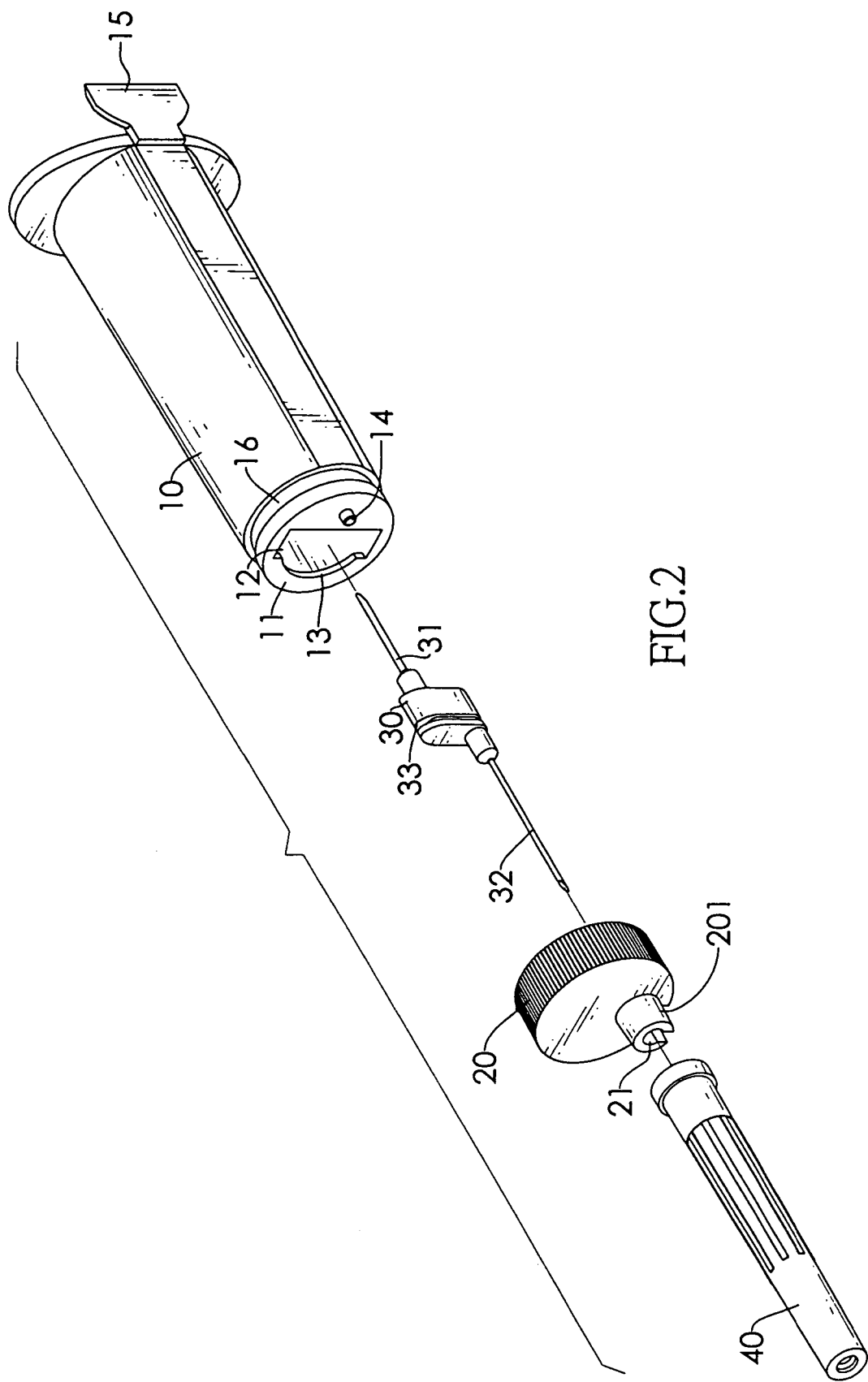
FIG. 2 is an exploded perspective view of the safety syringe for taking blood of the present invention.
Figure 3:
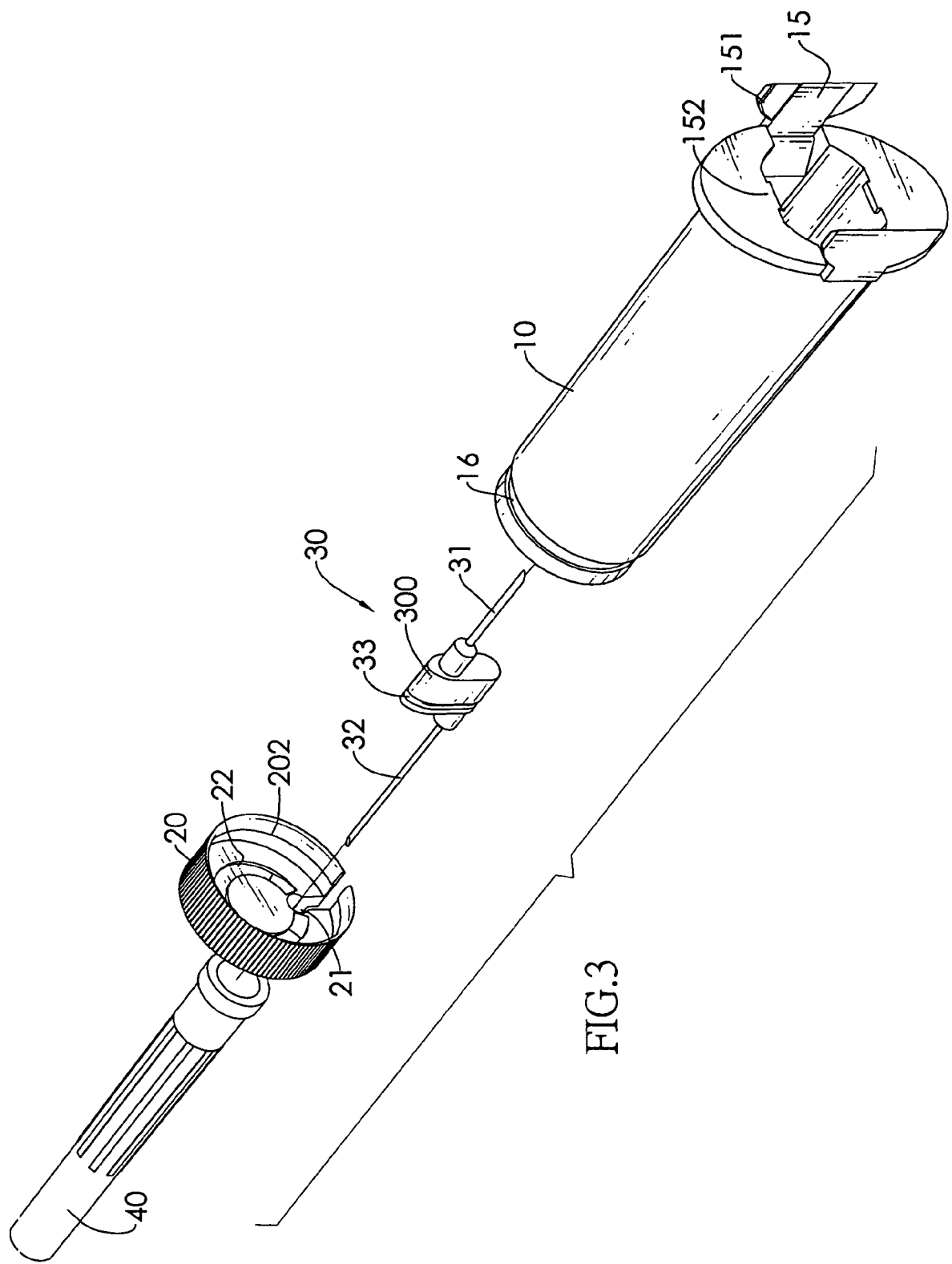
FIG. 3 is an exploded perspective view of the safety syringe for taking blood from a different angle.

With reference to FIGS. 1, 2 and 3, a safety syringe for taking blood in accordance with the present invention has a hollow barrel (10), a cap (20), a needle hub (30) and an enclosure (40).

The hollow barrel (10) is cylindrical and has a bottom open end and a top end with a board (11) integrally formed on a periphery defining the top end. A rectangular hole (12) is defined in the board (11) and a sectorial hole (13) is also defined in the board (11) to communicate with the rectangular hole (12). A stop (14) is formed on and extends out of the board (11) in a direction away from the interior of the hollow barrel (10). A bottom cap (15) is foldably attached to a periphery defining the bottom open end and a first rib (16) is formed on an outer periphery of the hollow barrel (10) near the top end.

The cap (20) is rotatably connected to the top end of the hollow barrel (10) and has an extension (201) extending from an outer side of the cap (20), a second rib (202) formed on an inner periphery of the cap (20) to correspond to the first rib (16) of the hollow barrel (10) such that after the cap (20) is mounted on the top end of the hollow barrel (10) and the second rib (202) extends over the first rib (16), the cap (20) is able to freely rotate relative to the hollow barrel (10), a notch (21) defined through a periphery of the cap (20) as well as the extension (201) and a guiding recess (22) defined inside the cap (20) to correspond to and receive therein the stop (14) of the hollow barrel (10).

The needle hub (30) has an elliptical body (300), a first needle (31) securely mounted on a rear side of the elliptical body (300) and a second needle (32) securely extending from a front side of the elliptical body (300). An annular recess (33) is defined in an outer periphery of the elliptical body (300).

The enclosure (40) is provided to close the second needle (32) after the needle hub (30) is mounted on the hollow barrel (10). The enclosure (40) is provided to enclose the second needle (32) for protection.

Figure 4:
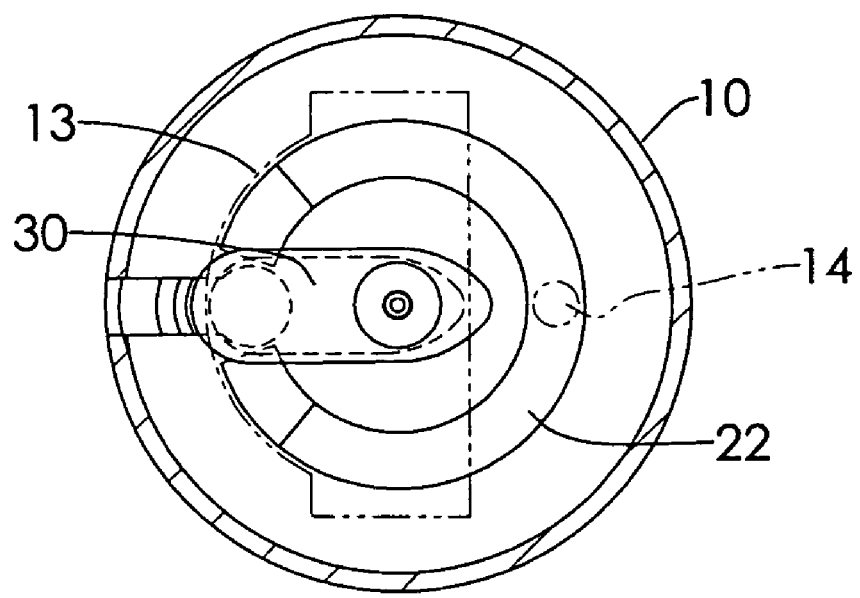
FIG. 4 is a schematic view showing that the needle hub is securely held in the barrel due to the configuration of the top open end of the barrel and the hollow elliptical body.
Figure 5:
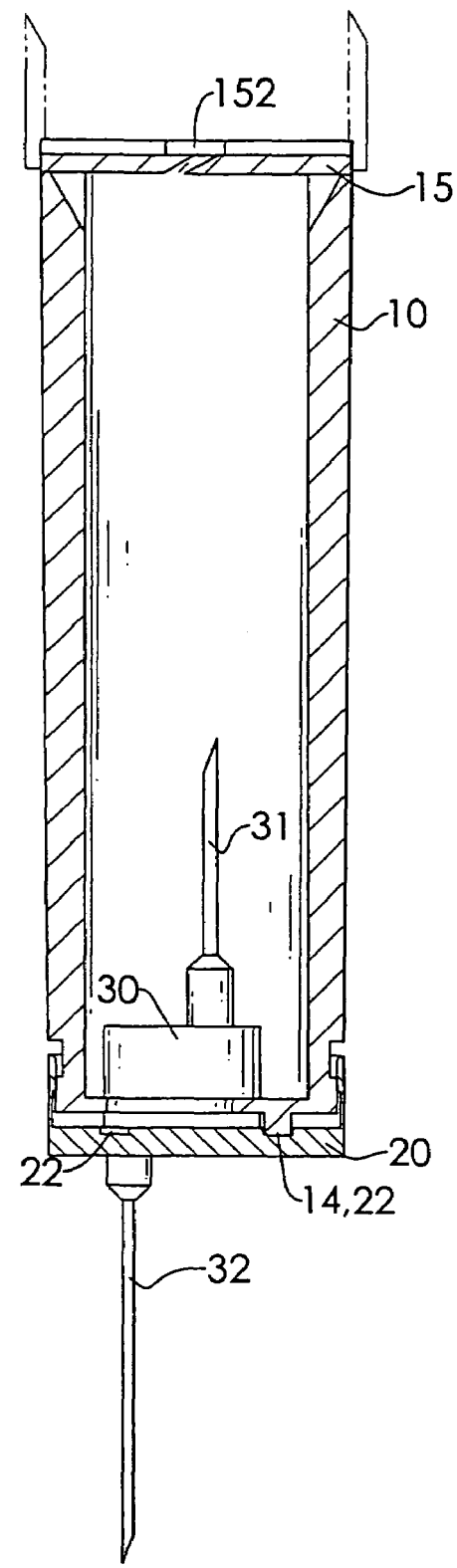
FIG. 5 is a cross sectional view showing that the needle hub is held inside the barrel.

When the safety syringe for taking blood is assembled, it is noted that the needle hub (30) is first combined with the cap (20) via extension of the second needle (32) out of the cap (20) via the notch (21) so that the cap (20) is able to securely hold the needle hub (30) inside the cap (20). Then the combination of the cap (20) and the needle hub (30) is connected to the hollow barrel (10). It is noted that because of the elliptical shape of the elliptical body (300), the elliptical body (300) has two long sides and two short sides sandwiched between the two long sides. Also, because of the rectangular shape of the hole (12), the rectangular hole (12) defines two long sides each having a length longer than that of the long side of the elliptical body (300) and two short sides each having a length longer than that of the short side of the elliptical body (300). However, the length of the long side of the elliptical body (300) is larger than a length of the short side of the rectangular hole (12) in combination with a depth of the sectorial hole (13). As a result of the length difference, the combination of the cap (20) and the needle hole (30) is able to be securely and rotatably mounted on the top of the hollow barrel (10) after the combination of the cap (20) and the needle hub (30) is rotated away from the original assembly position, as shown in FIGS. 4 and 5. That is, a side face defining the long side of the rectangular hole (12) and a side face defining the sectorial hole (13) are received in the annular recess (33) defined in the two opposite short sides of the elliptical body (300).

Meanwhile, due to the mutual abutment between the first rib (16) and the second rib (202), the cap (20) is securely engaged with the top end of the hollow barrel (10). In order to ensure the rotation of the cap (20) as well as the needle hub (30) relative to the hollow barrel (10) is smooth, the stop (14) is received in the corresponding guiding recess (22) so that the rotation of the cap (20) relative to the hollow barrel (10) will not be affected due to the addition of the needle hub (30) in that the elliptical body (300) is attached to one side of the cap (20) and the attachment of the needle hub (30) may shift the center of gravity, which may have an influence to the rotation of the cap (20) to the hollow barrel (10).

Figure 7:
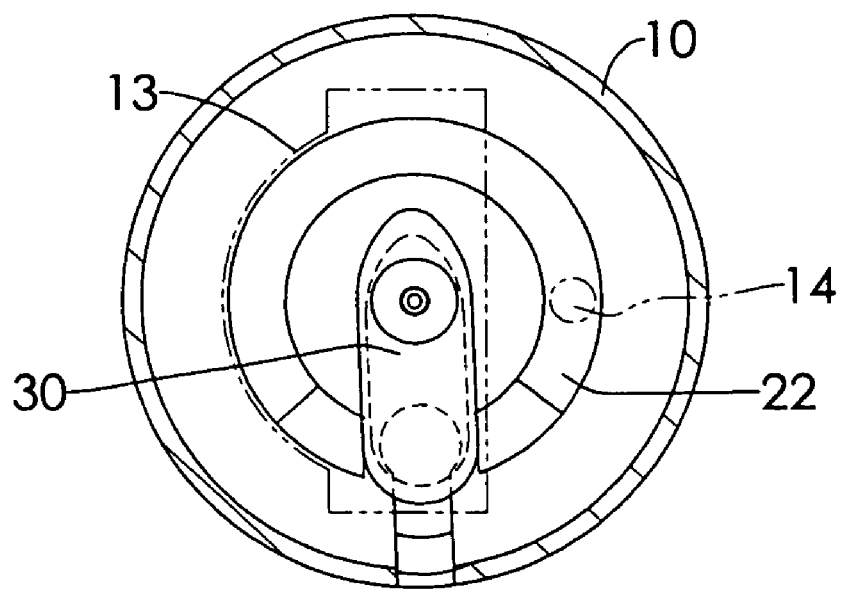
FIG. 7 is a schematic view showing that the needle is free from limitation of the configuration of the top open end of the barrel and ready to fall into the barrel.
Figure 6:
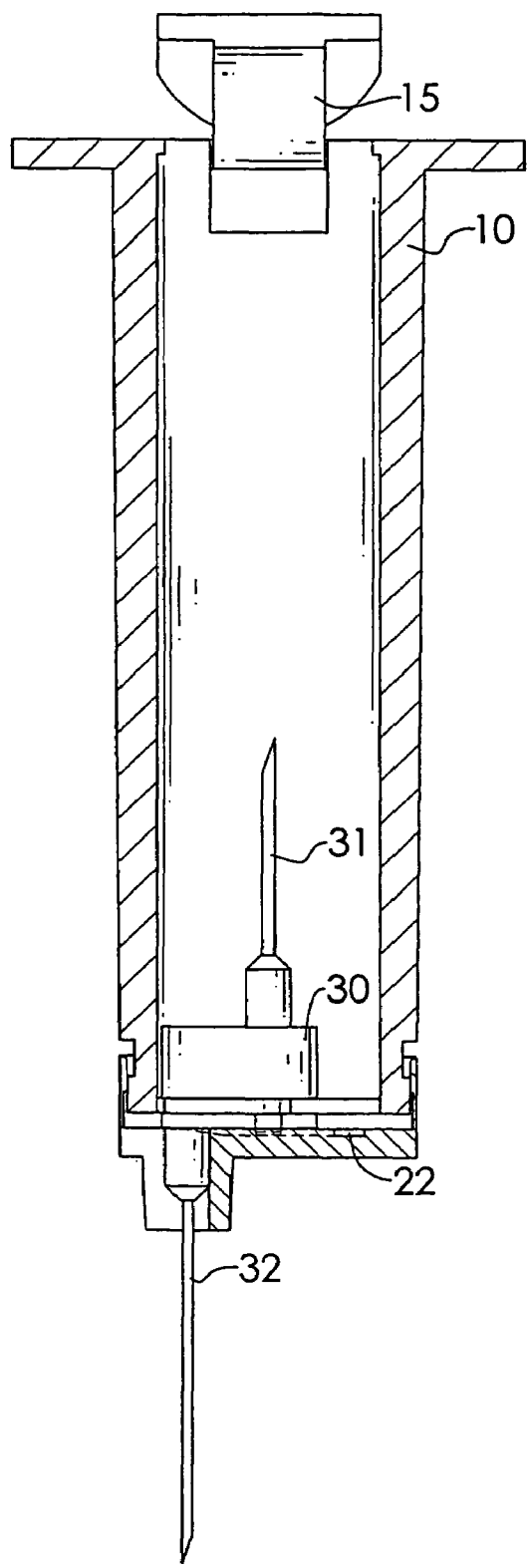
FIG. 6 is a cross sectional view showing that the needle hub is rotated inside the barrel for retrieval.
Figure 8:
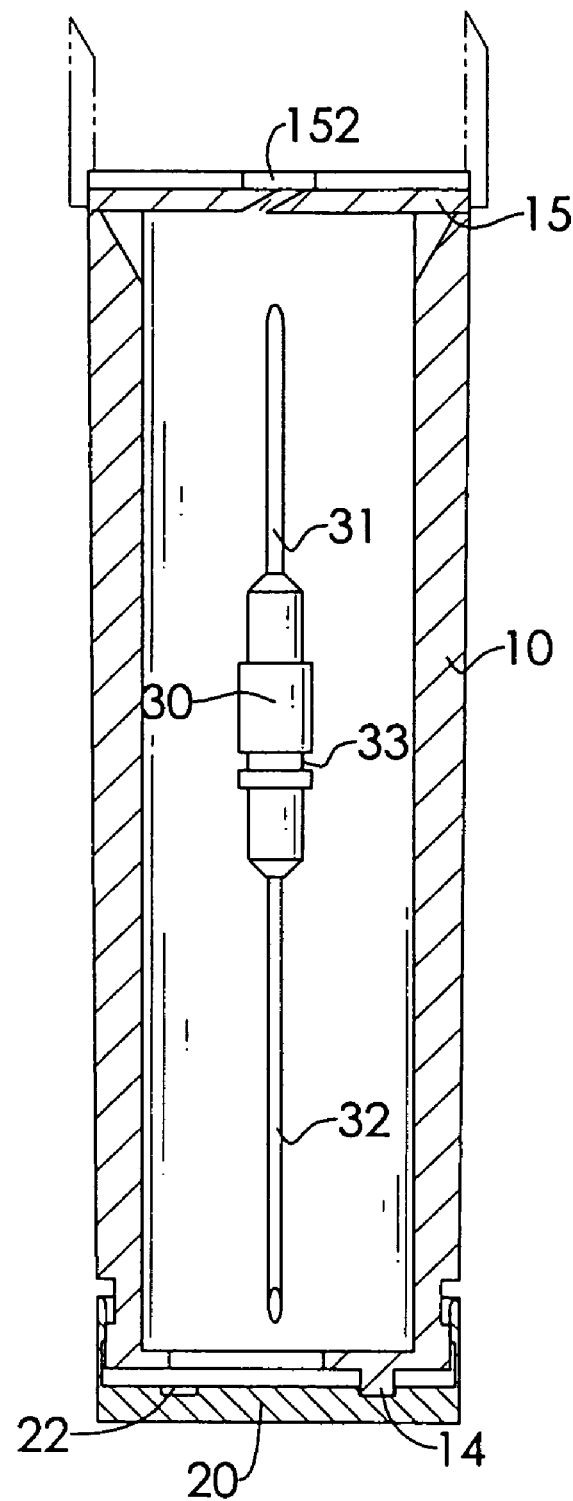
FIG. 8 is a cross sectional view showing that the needle hub is received in the barrel and the bottom cap is folded to close the bottom open end.

With reference to FIGS. 6, 7 and 8, after the second needle (32) is used to gather blood from the living creature, the user may rotate the combination of the cap (20) and the needle hub (30) again, which allows the long sides of the needle hub (30) to align with the long sides of the rectangular hole (12) of the hollow barrel (10). Therefore, the user may extend the needle hub (30) into the interior of the hollow barrel (10) for storage. Referring back to FIG. 5, it is noted that the bottom cap (15) on the bottom open end of the hollow barrel (10) is composed of two opposite halves each having a first boss (151) formed on two opposite sides of the bottom cap (15) to correspond to a second boss (152) formed on two opposite points defining the bottom open end of the hollow barrel (10). Therefore, after usage of the second needle (32) and before rotation of the cap (20) to align the long sides of the elliptical body (30) with the long sides of the rectangular hole (12) of the top end of the hollow barrel (10), the two halves of the bottom cap (15) are folded to allow the first bosses (151) to engage with the two second bosses (152) so as to close the bottom open end of the hollow barrel (10).

After the bottom open end of the hollow barrel (10) is closed, rotation of the cap (20) together with the needle hub (30) will align the needle hub (30) with the rectangular hole (12). Thus the needle hub (30) may be enclosed inside the hollow barrel (10) and accidental injury to the person who deal with the discarded waste is avoided.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe for taking blood comprising:
   a hollow barrel having a bottom open end, a top end, a rectangular hole defined in the top end to have two opposite long sides, two opposite short sides, and a stop formed on a side face of the top end;
   a needle hub detachably connected to at least one of the long sides of the rectangular hole and having a first needle extending from an elliptical body into an interior of the hollow barrel and a second needle extending away from the hollow barrel;
   a cap rotatably connected to the top end of the hollow barrel and having a notch defined through a periphery of the cap to receive therein the elliptical body so that the second needle extends out of the cap after in combination with the cap and the cap further having a guiding recess defined in an inner periphery thereof to correspond to and receive therein the stop to ensure smooth rotation of the cap relative to the hollow barrel; and
   an enclosure detachably enclosing the second needle for protection,
   whereby rotation of the cap as well as the needle hub aligns long sides of the elliptical body with the long sides of the rectangular hole such that the elliptical body together with the first needle and the second needle is able to extend into the interior of the hollow barrel for storage.

2. The safety syringe as claimed in claim 1, wherein the elliptical body has an annular recess defined in an outer periphery thereof so that the at least one long side of the rectangular hole is able to be received in the annular recess defined in the short sides of the elliptical body.

3. The safety syringe as claimed in claim 2, wherein the top end of the hollow barrel has a first rib formed on an outer periphery and the cap has a second rib formed on an inner periphery thereof such that after the cap is mounted to the top end, mutual abutment between the first rib and the second rib ensures that the cap is able to rotate freely relative to the hollow barrel.

4. The safety syringe as claimed in claim 1, wherein the top end of the hollow barrel has a first rib formed on an outer periphery and the cap has a second rib formed on an inner periphery thereof such that after the cap is mounted to the top end, mutual abutment between the first rib and the second rib ensures that the cap is able to rotate freely relative to the hollow barrel.

5. The safety syringe as claimed in claim 1, wherein the hollow barrel has a bottom cap foldably connected to a periphery defining the bottom open end so as to selectively close the bottom open end of the hollow barrel.

6. The safety syringe as claimed in claim 5, wherein the bottom cap is composed of two halves each having a first boss to correspond to two second bosses respectively formed on two opposite points of the periphery defining the bottom open end such that folding the bottom cap allows the first bosses to abut the second bosses and the bottom open end is closed.

* * * * *